(12) United States Patent
Sundaram et al.

(10) Patent No.: US 9,351,992 B2
(45) Date of Patent: May 31, 2016

(54) NON-ANTICOAGULANT POLYSACCHARIDE COMPOSITIONS

(75) Inventors: Mallikarjun Sundaram, Flemington, NJ (US); Takashi Kei Kishimoto, Lexington, MA (US); Sucharita Roy, Tyngsboro, MA (US)

(73) Assignee: MOMENTA PHARMACEUTICALS, INC., Cambridge, MA (US)

( * ) Notice: Subject to any disclaimer, the term of this patent is extended or adjusted under 35 U.S.C. 154(b) by 235 days.

(21) Appl. No.: 12/739,287

(22) PCT Filed: Nov. 3, 2008

(86) PCT No.: PCT/US2008/082224
§ 371 (c)(1),
(2), (4) Date: Aug. 6, 2010

(87) PCT Pub. No.: WO2009/059284
PCT Pub. Date: May 7, 2009

(65) Prior Publication Data
US 2010/0298260 A1    Nov. 25, 2010

Related U.S. Application Data

(60) Provisional application No. 60/985,080, filed on Nov. 2, 2007.

(51) Int. Cl.
| | |
|---|---|
| A61K 31/727 | (2006.01) |
| A01N 43/04 | (2006.01) |
| A61K 31/715 | (2006.01) |
| C08B 37/00 | (2006.01) |
| C08L 5/10 | (2006.01) |
| C12P 19/04 | (2006.01) |

(52) U.S. Cl.
CPC ........... *A61K 31/727* (2013.01); *C08B 37/0078* (2013.01); *C08L 5/10* (2013.01); *C12P 19/04* (2013.01)

(58) Field of Classification Search
CPC ..... A61K 31/727; C08B 37/0078; C08L 5/10
USPC .................................................. 514/54, 56
See application file for complete search history.

(56) References Cited

U.S. PATENT DOCUMENTS

| | | |
|---|---|---|
| 3,118,816 A | 1/1964 | Gushing et al. |
| 4,235,871 A | 11/1980 | Papahadjopoulos et al. |
| 4,303,651 A | 12/1981 | Lindahl et al. |
| 4,629,699 A | 12/1986 | Bianchini |
| 4,717,719 A | 1/1988 | Sportoletti et al. |
| 4,727,063 A | 2/1988 | Naggi et al. |
| 4,847,338 A | 7/1989 | Linhardt et al. |
| 4,868,103 A | 9/1989 | Stavrianopoulos et al. |
| 4,916,219 A | 4/1990 | Linhardt et al. |
| 4,990,502 A | 2/1991 | Lormeau et al. |
| 5,262,403 A | 11/1993 | Nicolson et al. |
| 5,264,425 A | 11/1993 | Dal Pozzo et al. |
| 5,296,471 A | 3/1994 | Holme et al. |
| 5,403,827 A | 4/1995 | De-Ambrosi |
| 5,541,166 A | 7/1996 | Parish et al. |
| 5,583,121 A | 12/1996 | Chaudry et al. |
| 5,668,116 A | 9/1997 | Cullis-Hill et al. |
| 5,668,118 A | 9/1997 | Kennedy |
| 5,690,910 A | 11/1997 | Ahmed et al. |
| 5,696,100 A | 12/1997 | Holme et al. |
| 5,707,974 A | 1/1998 | Kennedy |
| 5,733,893 A | 3/1998 | Ornitz |
| 5,763,421 A | 6/1998 | Caretto et al. |
| 5,767,269 A | 6/1998 | Hirsh et al. |
| 5,795,875 A | 8/1998 | Holme et al. |
| 5,808,021 A | 9/1998 | Holme et al. |
| 5,912,237 A | 6/1999 | Kennedy |
| 5,990,097 A | 11/1999 | Kennedy |
| 6,001,820 A | 12/1999 | Hirsh et al. |
| 6,077,683 A | 6/2000 | Kennedy |
| 6,127,347 A | 10/2000 | Chaudry et al. |
| 6,130,210 A | 10/2000 | Caretto et al. |
| 6,150,342 A | 11/2000 | Mattsson et al. |
| 6,545,136 B1 | 4/2003 | Hara et al. |
| 6,596,705 B1 | 7/2003 | Varki et al. |
| 7,781,416 B2 | 8/2010 | Casu et al. |
| 7,790,700 B2 | 9/2010 | Casu et al. |
| 8,067,555 B2 | 11/2011 | Casu et al. |
| 8,071,569 B2 | 12/2011 | Mousa |
| 8,569,262 B2 | 10/2013 | Sundaram et al. |
| 8,592,393 B2 | 11/2013 | Sundaram et al. |
| 2003/0013682 A1 | 1/2003 | Banito et al. |

(Continued)

FOREIGN PATENT DOCUMENTS

| | | |
|---|---|---|
| BE | 620906 | 11/1962 |
| CN | 1060599 A | 4/1992 |

(Continued)

OTHER PUBLICATIONS

Yamada, S., Murakami, t., Tsuda, H., Yoshida, K., Sugahara, K. (1995) Isolation of the Porcine Heparin Tetrasaccharides with Glucuronate 2-O-Sulfate. The Journal of Biological Chemistry, vol. 270, No. 15, p. 8696-8705.*

Mao, W., Thanawiroon, C., Linhardt, R.J. (2002) Capillary electrophoresis for the analysis of glycosaminoglycans and glycosaminoglycan-derived oligosaccharides. Biomedical Chromatography, vol. 16, p. 77-94.*

"Fragmin" by RxList: The Internet Drug Index. Retrieved on [Aug. 19, 2014] [online]. Retrieved from the internet at <http://www.rxlist.com/fragmin-drug.htm>.*

Linhardt, R.J., Gunay, N.S. (1999) Production and Chemical Processing of Low Molecular Weight Heparins. Seminars in Thrombosis and Hemostasis, vol. 25, suppl. 3, p. 5-16.*

(Continued)

*Primary Examiner* — Scarlett Goon
(74) *Attorney, Agent, or Firm* — Lando & Anastasi, LLP (57) ABSTRACT

Preparations of polysaccharides lacking substantial anticoagulant activity are provided herein. Methods of making and using such preparations are provided.

21 Claims, 1 Drawing Sheet

(56) References Cited

U.S. PATENT DOCUMENTS

| | | |
|---|---|---|
| 2003/0147848 A1 | 8/2003 | Geng |
| 2004/0056249 A1 | 3/2004 | Russell et al. |
| 2004/0087544 A1 | 5/2004 | Russo et al. |
| 2005/0107331 A1 | 5/2005 | Banito et al. |
| 2005/0137167 A1 | 6/2005 | Casu et al. |
| 2005/0222084 A1 | 10/2005 | Casu et al. |
| 2005/0282775 A1 | 12/2005 | Kennedy |
| 2006/0040896 A1 | 2/2006 | Kennedy |
| 2006/0172968 A1 | 8/2006 | Casu et al. |
| 2007/0037814 A1 | 2/2007 | Rawson et al. |
| 2007/0142323 A1 | 6/2007 | Viskov et al. |
| 2008/0051567 A1 | 2/2008 | Casu et al. |
| 2008/0280819 A1 | 11/2008 | Mulugeta et al. |
| 2009/0012165 A1 | 1/2009 | Ueno |
| 2009/0149424 A1 | 6/2009 | Byun et al. |
| 2010/0021416 A1 | 1/2010 | Lichter et al. |
| 2010/0081629 A1 | 4/2010 | Viskov et al. |
| 2010/0316640 A1 | 12/2010 | Sundaram et al. |
| 2010/0331746 A1 | 12/2010 | Deslandes |
| 2011/0076729 A1 | 3/2011 | Mamuwala et al. |
| 2011/0207919 A1 | 8/2011 | Beccati et al. |
| 2011/0288046 A1 | 11/2011 | Venkataraman et al. |

FOREIGN PATENT DOCUMENTS

| | | | |
|---|---|---|---|
| EP | 0121067 A1 | 10/1984 | |
| EP | 0346810 A2 | 12/1989 | |
| EP | 0557887 A2 | 9/1993 | |
| EP | 0735050 A2 * | 10/1996 | ............ C08B 37/10 |
| EP | 0735050 B1 | 10/1996 | |
| EP | 1129718 A2 | 9/2001 | |
| EP | 1268558 A1 | 1/2003 | |
| JP | 60115525 | 6/1985 | |
| JP | 2006501815 A | 1/2006 | |
| JP | 2007-517771 A | 7/2007 | |
| JP | 2008150441 A | 7/2008 | |
| JP | 2009538386 A | 11/2009 | |
| WO | 9012561 A1 | 11/1990 | |
| WO | 9201003 A1 | 1/1992 | |
| WO | 9202232 A1 | 2/1992 | |
| WO | 9217187 A1 | 10/1992 | |
| WO | 9217188 A1 | 10/1992 | |
| WO | 9218545 A1 | 10/1992 | |
| WO | 9629973 A2 | 10/1996 | |
| WO | 9842865 A1 | 10/1998 | |
| WO | 0155221 A1 | 8/2001 | |
| WO | 02083086 A1 | 10/2002 | |
| WO | 03022291 A1 | 3/2003 | |
| WO | 2007001409 A2 | 1/2007 | |
| WO | 2007014049 A2 | 2/2007 | |
| WO | 2007056218 A2 | 5/2007 | |
| WO | 2007059313 A1 | 5/2007 | |
| WO | 2007144144 A1 | 12/2007 | |
| WO | 2009007224 A1 | 1/2009 | |
| WO | 2009059283 A1 | 5/2009 | |
| WO | 2011130572 A1 | 10/2011 | |

OTHER PUBLICATIONS

Kennett, E.C., Davies, M.J. (2009) Glycosaminoglycans are fragmented by hydroxyl, carbonate, and nitrogen dioxide radicals in a site-selective manner: implications for peroxynitrite-mediated damage at sites of inflammation. Free Radical Biology & Medicine, vol. 47, p. 389-400.*
International Preliminary Report on Patentability for PCT/US2008/082223 filing date Nov. 3, 2008.
Written Opinion of the International Seraching Authority for PCT/US2008/082223.
International Search Report for PCT/US2008/082223 mailing date Jan. 28, 2009.
International Search Report for PCT/US2011/32581 filing date Apr. 14, 2011.
Written Opinion of the International Seaching Authority for PCT/US2011/32851 mailing date Jul. 5, 2011.
Casu et al., "Non-Anticoagulant Heparins and Inhibition of Cancer", Pathophysiol Haemost Thromb., vol. 36, pp. 195-203 (2007).
Naggi et al., "Modulation of the Heparanase-inhibiting Activity of Heparin through Selective Desulfation, Graded N-Acetylation, and Glycol Splitting", The Journal of Biological Chemistry, vol. 280, No. 13, pp. 12103-12113 (2005).
Pisano et al., "Undersulfated, low-molecular-weight glycol-split heparin as an antiangiogenic VEGFantagonist" Glycobiology, vol. 15, No. 2, pp. 1C-6C. (2005).
Sasisekharan et al., "Roles of Heparin-Sulphate Glycosaminoglycans in Cancer", Nature Reviews, vol. 2, pp. 521-528 (2002).
Casu et al., "Undersulfated and Glycol-Split Heparins Endowed with Antiangiogenic Activity", J. Med. Chem., vol. 47, pp. 838-848 (2004).
Casu et al., "Short Heparin Sequences Spaced by Glycol-Split Uronate Residues Are Antagonists of Fibroblast Growth Factor 2 and Angiogenesis Inhibitors", Biochemistry, vol. 41, pp. 10519-10528 (2002).
Casu et al., "Retention of Antilipemic Activity by Periodate-oxidized Non-anticoagulant Heparins", Arseneimittel Forschung/Drug Res. vol. 36 (1), No. 4, pp. 637-642 (1986).
Hrivocini, et al., "Active Conformation of Glycosaminoglycans. NMR Determination of the Conformation of Heparin Sequences Complexed with Antithrombin and Fibroblast Growth Factors in Solution", Seminars in Thrombosis and Hemostasis, vol. 28, No. 4, pp. 325-333 (2002).
Casu et al., "Chemical Derivatization as a Strategy to Study Structure-Activity Relationships of Glycosaminoglycans", Seminars in Thrombosis and Hemostasis, col. 28, No. 4, pp. 335-342 (2002).
Mascellani et al., "Structure and Contribution to the heparin cofactor II-mediated inhibition of thrombin of naturally oversulphated sequences of dermatan sulphate" Biochem. J. vol. 296 pp. 639-648 (1993).
Kragh et al., "Non-anti-coagulant heparin inhibits metastasis but not primary tumor growth", Oncology Reports, vol. 14, pp. 99-104 (2005).
Icli et al., "Low moelecular weight heparin (LMWH) increase the efficacy of cisplatinum plus gemcitabine combination in advanced pancreatic cancer", J. Surg Oncol., vol. 95 (6), pp. 507-512 (2007) Abstract Only.
Fransson et al., "Relationship between anticoagulant activity of heparin and susceptibility to periodate oxidation", Department of Physiological Chemsitry, vol. 97, No. 1, pp. 119-123 (1979).
Peters et al., "Randomized comparison of a novel anticoagulant, vasoflux, and heparin as adjunctive therapy to streptokinase for acute myocardial infarction(vasoflux international trial for acute myocardial infarction lysis)", American Heart Journal., vol. 142 (2), pp. 237-243 (2001).
Ritchie et al., "A chemically modified heparin, inhibits myeloma growth and angiogenisis via disruption of the heparanase/syndecan-1 axis", Clin Can Res, pp. 1382-1393 (2011).
Spickler et al., "Clinical evaluation of the pharmacology, and safety of vasoflux[trademark symbol], a novel antithrombotic", Abstracts from the 70th scientific sessions, Nov. 9-12, 1997.
Weitz et al., "Vasoflux, a new anticoagulant with a novel mechanism of action", circ.ahajournals.org, pp. 682-689 (1999).
Yang et al., "Targeting heparanase as a therapy for multiplemyeloma", Abstract # 257, Apr. 18, 2009.
Chinese Search Report from Chinese Application No. 201180019382.7 dated Jun. 7, 2014.
Apsner et al., "Dalteparin-induced alopecia in hemodialysis patients: reversal by regional cirate anticoagulate as an example" Blood, vol. 97(9) pp. 2914-2915 (2001).
Bassas P et al., "Anticoagulation and Antiplatelet Therapy in Dermatology", ACTAS DERMOSIFILIOGRAFICAS, vol. 100, No. 1, pp. 7-16 (2009).
Chu et al., "M-ONC 402, a novel low molecular weight heparin (LMWH) interacts with heparin-binding proteins and inhibits metastatic seeding of tumor cells in mice", Proceedings of the American Association for Cancer Research Annual Meeting, vol. 50 p. 1210 (2009).

(56) References Cited

OTHER PUBLICATIONS

De Lorenzo Ferruccio et al: "The role of anticoagulation in cancer patients: Facts and figures" Anti-Cancer Agents in Medicinal Chemistry, vol. 6, No. 6, pp. 579-587 (2006).
Derbyshire et al., "Anti-tumor and Anti-angiogenic effects in Mice of Heparin Conjugated to Angiostatic Steriods" Int. J. Cancer vol. 63 pp. 694-701 (1995).
Diaz-Montero et al., "Increased circulating myeloid-derived suppressor cells correlate with clinical cancer stage, mestastatic tumor burden, and doxorubicin-cyclophosphamide chemotherapy", Cancer Immunology Immunotherapy, vol. 58, No. 1 pp. 49-59 (2009).
Extended European Search Report from European Application No. 11769624.5 dated Jun. 26, 2013.
Extended European Search Report from European Application No. 11769718.5 dated Jul. 12, 2013.
Ferro Vito et al: "PI-88 and novel heparan sulfate mimetics inhibit angiogenesis" Seminars in Thrombosis and Hemostasis, vol. 33, No. 5, pp. 557-562 (2007).
Gabrilovich Dmitry I et al: "Myeloid-derived suppressor cells as regulators of the immune system" Nature Reviews Immunology, vol. 9, No. 3, pp. 162-174 (2009).
Gerotziafas G T et al: "Clinical studies with anticoagulants to improve survival in cancer patients" Pathophysiology of Haemostasis and Thrombosis 2008 S. Karger AG CHE LNKD-DOI:10.1159/000175158, vol. 36, No. 3-4, pp. 204-211 (2008).
Goodman and Gilman's, "The Pharmacological Basis of Therapeutics" published by The McGraw-Hill Companies, Inc. pp. 5-8, 2001.
He Zhou et al., "M-ONC 402—a non anticoagulant low molecular weight heparin inhibits tumor metastasisHe", Proceedings of the American Association for Cancer Research Annual Meeting, p. 69 (2009).
International Prelimnary Report of Patentability and Written Opinion from International Application Serial No. PCT/US2008/082224 mailed Feb. 4, 2010.
International Search Report for PCT/US2011/32771 Nov. 23, 2011.
International Search Report including Written Opinion for PCT/US2011/040470 mailed Oct. 16, 2012.
Johnson et al., "Can Cancer Tumors Be Starved to Death"? Retrieved Sep. 20, 2012 (online) <http://www.mhhe.com/biosci/genbio/tlw3/virtual_labs/lab6/labs/resources/original.pdf>.
Kondo et al., "Favorable Prognosis of Renal Cell Carcinoma with Increased Expression of Chemokines Associated with a Th1-type Immune Response," Cancer Science, 2006, vol. 97, Iss. 8, pp. 780-786.
Matsumoto et al., "Granulocyte-colony Stimulating Factor-producing Esophageal Carcinoma: Serum Level as a Marker for Monitoring the Effects of Treatment," International Journal of Clinical Oncology, 2000, vol. 5, Iss. 5, pp. 328-333.
Mousa Shaker A: "Role of current and emerging antithrombotics in thrombosis and cancer" Drugs of Today, vol. 42, No. 5, pp. 331-350 (2006).
Ostrand-Rosenberg Suzanne et al: "Myeloid-Derived Suppressor Cells: Linking Inflammation and Cancer" Journal of Immunology, vol. 182, No. 8, pp. 4499-4506 (2009).
Addison, et al., "The CXC Chemokine, Monokine Induced by Interferon-gamma, Inhibits Non-Small Cell Lung Carcinoma Tumor Growth and Metastasis" Human Gene Therapy, 11:247-261 (2000).
Hilbe, et al., "CD133 positive endothelial progenitor cells contribute to the tumour vasculature in non-small cell lung cancer" J Clin Pathol, 57:965-969 (2004).
Kragh, et al., "Non-anti-coagulant heparins: A promising approach for prevention of tumor metastasis (Review)" International Journal of Oncology, 27:1159-1167 (2005).
Lolkema, et al., "Abstract LB-43:M402, a novel heparin sulphate mimetic, synergizes with gemcitabine to improve survival and reduce metastasis and epithelial-to-mesenchymal transition (EMT) in a genetically engineered mouse model for pancreatic cancer" Cancer Research, 70(8 Suppl): Abstract LB-43 (2010).
Natori, et al., "G-CSF stimulates angiogenesis and promotes tumor growth: potential contribution of bone marrow-derived endothelial progenitor cells" Biochemical and Biophysical Research Communications, 297:1058-1061 (2002).
Yamashita, et al., "Immunoreactive Hepatocyte Growth Factor is a Strong and Independent Predictor of Recurrence and Survival in Human Breast Cancer" Cancer Research, 54:1630-1633 (1994).
Yao, et al., "Multiple signaling pathways involved in activation of matrix metalloproteinase-9 (MMP-9) by heregulin-beta1 in human breast cancer cells" Oncogene, 20:8066-8074 (2001).
Zea, et al., "Arginase-Producing Myeloid Suppressor Cells in Renal Cell Carcinoma Patients: A Mechanism of Tumor Evasion" Cancer Res., 65(8):3044-3048 (2005).
Zhou, et al., "Abstract #281: M-ONC 402—a non anticoagulant low molecular weight heparin inhibits tumor metastasis" Cancer Research, 69:Abstract 281 (2009).
Avci et al., "Synthetic Oligosaccharides as Heparin-Mimetics Displaying Anticoagulant Properties" Current Pharm. Design, 9:2323-2335 (2003).
Beccati et al., "Identification of a novel structure in heparin generated by potassium permanganate oxidation" Carbohydrate Polymers, 82:699-705 (2010).
Beyer, et al., "Composition of OSCS-contaminated heparin occurring in 2008 in batches on the German market" European Journal of Pharmaceutical Sciences, 40:297-304 (2010).
Cui et al., "Structure Analysis of Polysaccharides" Food Carbohydrates: Chemistry, Physical Properties and Applications (2005), Section 3.3.2.1 and 3.3.2.2 only.
Gerotziafas et al., "Effect of the anti-factor Xa and anti-factor IIa activities of low-molecular-weight heparins upon the phases of thrombin generation" Journal of Thrombosis and Haemostasis, 5:955-962 (2007).
Gray et al., "Heparin and Low-molecular-weight heparin" Thromb. Haemost vol. 99, pp. 807-818 (2008).
Halsall et al., "Oxidation of Carbohydrate by the Periodate Ion" Journal of Chemical Society, 172:1427-1432 (1947).
International Prelimnary Report of Patentability and Written Opinion from International Application Serial No. PCT/US2010/031480 mailed Oct. 18, 2011.
International Prelimnary Report of Patentability and Written Opinion from International Application Serial No. PCT/US2011/032581 mailed Oct. 16, 2012.
International Prelimnary Report of Patentability and Written Opinion from International Application Serial No. PCT/US2011/032771 mailed Oct. 16, 2012.
International Search Report for PCT/US2008/082224 mailing date May 20, 2009.
International Search Report for PCT/US2010/031480 mailing date Sep. 27, 2010.
International Search Report for PCT/US2011/032581 mailing date Jul. 5, 2011.
International Search Report for PCT/US2014/039538 mailing date Oct. 1, 2014.
International Search Report for PCT/US2014/039542 mailing date Oct. 1, 2014.
Lifespan, "Low Molecular Weight Heparin (LMWH) ELISA Kit for Buffer/Urine Samples" Mar. 8, 2013.
Sakuma et al., "Particulate Phase of Cellulose Cigarrette Smoke" Agric. Biol. Chem., 44(3):555-561 (1980).
Ansel, H.C., Allen, Jr., L.V., Popovich, N.G. (1999) Pharmaceutical Dosage Forms and Drug Delivery Systems, published by Lippincott Williams & Wilkins, p. 48-53 and 120-128.
Gradishar, W.J. (2006) Albumin-bound paclitaxel: a next-generation taxane. Expert Opinion in Pharmacotherapy, vol. 7, No. 8, p. 1041-1053.
Koliopanos, A., Friess, H., Kleef, J., Shi, X., Liao, Q., Peeker, I., Vlodaysky, I., Zimmermann, A., Buchler, M.W. (2001) Heparanase Expression in Primary and Metastatic Pancreatic Cancer. Cancer Research, vol. 61, p. 4655-4659.
Safran, H., Dipetrillo, T., Iannitti, D., Quirk, D., Akerman, P., Gruff, D., Cioff, W., Shah, S., Ramdin, N., Rich, T. (2002) International Journal of Radiation Oncology Biology Physics, vol. 54, No. 1, p. 137-141.

* cited by examiner

NON-ANTICOAGULANT POLYSACCHARIDE COMPOSITIONS

CROSS-REFERENCE TO RELATED APPLICATIONS

This application is a national stage application under 35 U.S.C. §371 of International Application No.: PCT/US2008/082224, filed Nov. 3, 2008, which claims the benefit under 35 USC §119(e) of U.S. provisional application 60/985,080, filed Nov. 2, 2007.

BACKGROUND

Heparin, a highly sulfated heparin-like glycosaminoglycan (HLGAG) produced by mast cells and isolated from natural sources, is a widely used clinical anticoagulant. However, the effects of natural, or unfractionated, heparin can be difficult to predict and patients must be monitored closely to prevent over- or under-anticoagulation. Low molecular weight heparins (LMWHs) obtained by various methods of fractionation or depolymerization of polymeric heparin have more predictable pharmacological action as anticoagulants, reduced side effects, sustained antithrombotic activity, and better bioavailability than unfractionated heparin (UFH). Several LMWHs are approved for outpatient treatment of thrombotic conditions.

There is increasing interest in the potential role of antithrombotic agents in the management of cancer patients. Results from several recent clinical trials have suggested a survival advantage for certain types of cancer patients treated with LMWHs (reviewed in Lemoine, 2005, *Journal of Clinical Oncology*, 23: 2119-20).

SUMMARY OF THE INVENTION

The invention is based, in part, on the development of polysaccharide preparations, e.g., preparations of polysaccharides derived from heparin, that lack substantial anticoagulant activity (e.g., have substantially no anticoagulant activity) but retain activity in other non-coagulation mediated biological processes, and methods to produce them. These compounds can have one or more of the following features: 1) an anti-Xa activity and an anti-IIa activity each less than 50 IU/mg, and 2) anti-metastatic, anti-angiogenic, anti-fibrotic and/or anti-inflammatory activity. The polysaccharides disclosed herein can also have structural characteristics that distinguish them from other polysaccharides, (e.g., from commercially available heparins). For example, a polysaccharide preparation provided herein can have one or more of the following characteristics: the preparation has a weight average molecular weight between 3,500 and 7,000 Da; the preparation has substantially no modified hexosamine or uronic acid residues, e.g., substantially no glycol split uronic acid residues; the preparation has greater than 40% $U_{2S}H_{NS,6S}$ disaccharide residues; degree of desulfation of the preparation less than 40%; one or more polysaccharide chains of the preparation has a 4,5-unsaturation of a non-reducing end uronic acid residue; and the preparation has less than 10% of the tetrasaccharide —$UH_{NAc,6S}GH_{NS,3S,6S}$. This disclosure includes preparations having one or more of these properties and characteristics as well as methods of making and using such preparations.

Accordingly, in a first aspect, the invention features a polysaccharide preparation (e.g., a heparin-derived preparation) that includes (e.g., consists essentially of) polysaccharides of Formula I:

wherein n is an integer such that n=1-20 (e.g., 1-10, 1-11, 1-12, 1-13, 1-14, 1-15, 1-16, 1-17, 1-18, or 1-19); w=−2OS or −2OH; x=−NS or −NAc; y=−3OS or −3OH; z=−6OS or −6OH;

wherein U indicates an uronic acid residue and H indicates a hexosamine residue; and wherein w, x, y, and z are the same or different on each U or H residue.

In a second aspect, the invention features a polysaccharide preparation (e.g., a heparin-derived preparation) having a weight average molecular weight between 3,500 and 7,000 Da (e.g., between 3,500 and 5,000 Da) and reduced (e.g., substantially no) anticoagulant activity, wherein the preparation includes (e.g., consists essentially of) polysaccharides comprising Formula I:

wherein n is an integer such that n=1-20 (e.g., 1-10, 1-11, 1-12, 1-13, 1-14, 1-15, 1-16, 1-17, 1-18, or 1-19); w=−2OS or −2OH; x=−NS or −NAc; y=−3OS or −3OH; z=−6OS or −6OH;

wherein U indicates an uronic acid residue and H indicates a hexosamine residue; and wherein w, x, y, and z are the same or different on each U or H residue.

In a third aspect, the invention features a polysaccharide preparation (e.g., a heparin-derived preparation) lacking substantial (e.g., having substantially no) anticoagulant activity, wherein the preparation consists essentially of polysaccharides of Formula I:

wherein n is an integer such that n=1-20 (e.g., 1-10, 1-11, 1-12, 1-13, 1-14, 1-15, 1-16, 1-17, 1-18, or 1-19); w=−2OS or −2OH; x=−NS or −NAc; y=−3OS or −3OH; z=−6OS or −6OH;

wherein U indicates a uronic acid residue and H indicates a hexosamine residue; wherein w, x, y, and z are the same or different on each U or H residue, and wherein the composition has an anti-Xa activity and an anti-IIa activity each less than 50 IU/mg (e.g., an anti-Xa activity less than about 45 IU/mg, 40 IU/mg, 35 IU/mg, 30 IU/mg, 25 IU/mg, or 20 IU/mg and an anti-IIa activity less than about 40 IU/mg, 30 IU/mg, 20 IU/mg, 15 IU/mg, 10 IU/mg, or 5 IU/mg).

In a fourth aspect, the invention features a polysaccharide preparation (e.g., a heparin-derived preparation) having the following characteristics: (a) weight average molecular weight between 3,500 and 7,000 Da (e.g., between 3,500 and 5,000 Da); (b) an anti-Xa activity and an anti-IIa activity each less than 50 IU/mg (e.g., an anti-Xa activity less than about 45 IU/mg, 40 IU/mg, 35 IU/mg, 30 IU/mg, 25 IU/mg, or 20 IU/mg and an anti-IIa activity less than about 40 IU/mg, 30 IU/mg, 20 IU/mg, 15 IU/mg, 10 IU/mg, or 5 IU/mg); and (c) substantially no (e.g., less than 5%, 4%, 3%, 2%, 1%, or no) glycol split uronic acid residues are present in the preparation.

The invention also includes pharmaceutically acceptable salts of any of the preparations described herein (e.g., described above) and compositions (e.g., pharmaceutical compositions) that comprise the preparations described herein and/or their pharmaceutically acceptable salts.

Any of the preparations described herein, e.g., described above, can have other properties. E.g., one of the above described preparations or pharmaceutical compositions can further have one or more of the functional or structural properties set out below.

In one embodiment, the preparation has a weight average molecular weight between 3,500 and 7,000 Da (e.g., between 3,500 and 6,000 Da; between 3,500 and 5,500 Da; between 3,500 and 5,000 Da; between 4,000 and 6,000 Da; between 4,000 and 5,500 Da; between 4,000 and 5,000 Da; between 4,500 and 5,500 Da; between 4,500 and 5,000 Da).

In one embodiment, the preparation has an anti-Xa activity and an anti-IIa activity each less than 50 IU/mg (e.g., an anti-Xa activity less than about 45 IU/mg, 40 IU/mg, 35 IU/mg, 30 IU/mg, 25 IU/mg, or 20 IU/mg and an anti-IIa activity less than about 40 IU/mg, 30 IU/mg, 20 IU/mg, 15 IU/mg, 10 IU/mg, or 5 IU/mg)

In one embodiment, the preparation includes more than 40% $U_{2S}H_{NS,6S}$ disaccharide residues (e.g., greater than 50%, 60%, 70%, or 80% $U_{2S}H_{NS,6S}$ disaccharide residues).

In one embodiment, the preparations include polysaccharide chains having a degree of desulfation less than 40% (e.g., less than 30%, 20%, or 10%). The degree of desulfation, as used herein, is defined as the percent reduction in moles of sulfate per moles of disaccharide unit as compared to unfractionated heparin.

In one embodiment, the preparations include polysaccharide chains having a degree of sulfation greater than or equal to 1.2, 1.4, 1.6, 1.8, 2.0, 2.2, 2.4, or 2.6. The degree of sulfation, as used herein, is defined as the average number of moles of sulfate per moles of disaccharide unit.

In one embodiment, at least one of the polysaccharide chains in the preparation or composition has a 4,5-unsaturation at the non-reducing end (e.g., as a result of heparinase digestion or benzyl esterification followed by beta-elimination). For example, about 10%, 20%, 30%, 40%, 50%, 60%, 70%, 80%, 90%, or substantially all of the non-reducing uronic acids in the preparation or composition have a 4,5-unsaturation.

In one embodiment, the preparation or composition includes a lower level of —$UH_{NAc,6S}GH_{NS,3S,6S}$ than enoxaparin, dalteparin, and/or UFH. E.g., the preparation of composition includes about 0 to 4 mole %, e.g., 0 to 3 mole %, e.g., 0 to 2 mole % of —$UH_{NAc,6S}GH_{NS,3S,6S}$.

In one embodiment, about 10-40% (e.g., about 10-35%, about 10-30%, about 15-35%, about 15-30%, about 20-35%, about 20-30%) of the polysaccharide chains of the preparation include the pentasaccharide $H_{NAc,6S}GH_{NS,3S,6S}I_{2S}H_{NS,6S}$.

In one embodiment, the preparation includes about 10-40% (e.g., about 10-35%, about 10-30%, about 15-35%, about 15-30%, about 20-35%, about 20-30%) of the polysaccharide chains having the tetrasaccharide —$U_{2S}H_{NAc,6S}GH_{NS,3S,6S}$.

In one embodiment, the preparation has substantially no (e.g., less than 5%, 4%, 3%, 2%, 1%, or no) glycol split uronic acid residues.

In one embodiment, the preparation or composition has a molecular weight distribution such that 10-50% (e.g., 20-50%, 20-45%, 25-50%, 25-45%, 30-50%, 30-45%, or 35-45%) of the oligosaccharides of the preparation have a molecular weight <3000 Da; 40-65% (e.g., 40-60%, 40-55%, or 40-50%) of the oligosaccharides have a molecular weight between 3000-8000 Da, and 5-30% (e.g., 5-25%, 5-20%, 5-15%, 10-25%, or 10-20%) of the oligosaccharides have a molecular weight >8000 Da.

In one embodiment, the preparation has a polydispersity of about 1.6 to 2.1 (e.g., about 1.6 to 2.0, about 1.7 to 2.0, about 1.6 to 1.9, about 1.7 to 1.9).

In one embodiment, the preparation or composition has significant anti-metastatic activity.

In one embodiment, the preparation or composition binds specifically to or inhibits an activity of one or more of: VEGF, FGF, SDF-1 or P-selectin.

In one embodiment, the preparation or composition has a calcium content less than 3%, 2.5%, 2%, 1.5%, 1.0%, and/or a sodium content less than 30%, 25%, 20%, 15%, 10%. In one embodiment, the preparation or composition comprises: less than 1000 ng/mg, 750 ng/mg, 500 ng/mg, 250 ng/mg of a heparinase enzyme, e.g., a heparinase enzyme described herein; less than about 1.0%, 0.5%, 0.3% w/w methanol; and less than 2.0%, 1.75%, 1.25%, 1.0%, 0.5%, 0.3%, 0.15% chloride.

In another aspect, the invention features methods of making a polysaccharide preparation. The methods include digesting an UFH with an enzyme that cleaves at the pentasaccharide $H_{NAc/S,6S}GH_{NS,3S,6S}I_{2S}H_{NS,6S}$ (e.g., at the linkage between the $H_{NS,3S}$ and $I_{2S}$ residues) and/or cleaves a $I_{2S}H_{NS}$ or $I_{2S}H_{AC}$ disaccharide. In some embodiments, the enzyme is a heparinase enzyme (e.g., *Bacteroides thetaiotaomicron* Heparinase I).

In another aspect, methods of making a preparation include: (1) digesting UFH with a heparinase enzyme that cleaves at the pentasaccharide $H_{NAc/S,6S}GH_{NS,3S,6S}I_{2S}H_{NS,6S}$ (e.g., at the linkage between the $H_{NS,3S}$ and $I_{2S}$ residues), and/or cleaves a $I_{2S}H_{NS}$ or $I_{2S}H_{AC}$ (e.g., *B. thetaiotaomicron* Heparinase I); (2) monitoring absorbance at 232 nm during the step of digesting; and (3) stopping (e.g., quenching) the digestion reaction when the absorbance at 232 nm is between 1.7 and 2.0. In one embodiment, the heparinase enzyme is present at about 1.0 to 5.0 IU/g UFH. In one embodiment, the step of digesting does not include treatment of the digestion reaction with a thiol reducing agent (e.g., dithiothreitol (DTT), 2-mercaptoethanol, or the like).

In another aspect, the invention features methods of manufacturing a polysaccharide preparation. The methods include: (1) digesting an unfractionated heparin (UFH) with a heparinase enzyme that cleaves at the pentasaccharide $H_{NAc/S,6S}GH_{NS,3S,6S}I_{2S}H_{NS,6S}$, e.g., cleaves at the linkage between the $H_{NS,3S}$ and $I_{2S}$ residues and/or cleaves a $I_{2S}H_{NS}$ or $I_{2S}H_{AC}$, (e.g., *Bacteroides thetaiotaomicron* Heparinase I), to yield a polysaccharide; and (2) isolating the polysaccharide (e.g., by precipitating with a salt and a polar organic solvent), to thereby make a polysaccharide preparation.

In one embodiment, the step of digesting includes treating the UFH with the enzyme (e.g., at about 1.0 to 5.0 IU/g UFH); monitoring absorbance at 232 nm during the step of digesting; and stopping (e.g., quenching) the digestion reaction when the absorbance at 232 nm reaches between 1.7 and 2.0. In one embodiment, the step of digesting does not include treatment of the digestion reaction with a thiol reducing agent (e.g., dithiothreitol (DTT), 2-mercaptoethanol, or the like).

In one embodiment, the preparation is evaluated for a biological activity, e.g., anti-metastatic activity; binding to any of VEGF, FGF, SDF-1, and P-selectin; or inhibition of an activity of any of VEGF, FGF, SDF-1, and P-selectin.

In another aspect, the invention features a polysaccharide preparation made by a method described herein.

In another aspect, the invention includes an intermediate or reaction mixture from any of the methods for making or analyzing a polysaccharide preparation described herein.

In another aspect, the invention features a pharmaceutical composition that includes a polysaccharide preparation described herein.

In one embodiment, the pharmaceutical composition further includes a pharmaceutically acceptable carrier.

In another aspect, the invention features a method of treating a subject that includes administering a therapeutically effective amount of a polysaccharide preparation disclosed herein to the subject. The terms "treating," "treatment," and the like, mean administering the preparation to a subject or a cell or tissue of a subject in order to obtain a desired pharmacological, physiological or clinical effect. Treatment with a polysaccharide preparation described herein may lessen, reduce, mitigate, ameliorate, delay, or prevent an existing unwanted condition or the onset or a symptom thereof. A "therapeutically effective amount" refers to an amount effective, at dosages and for periods of time necessary, to achieve the desired pharmacological, physiological or clinical effect in the subject.

The invention includes methods for treating a subject having, or at risk of having, a metastatic disorder (e.g., a cancer, e.g., a carcinoma or other solid cancer). In those subjects, treatment may include, but is not limited to, inhibited tumor growth, reduction in tumor mass, reduction in size or number of metastatic lesions, inhibited development of new metastatic lesions, prolonged survival, prolonged progression-free survival, prolonged time to progression, and/or enhanced quality of life. In another embodiment, the subject may have a disorder or condition selected from the group consisting of: an inflammatory disorder, an autoimmune disease, a fibrotic or fibroproliferative disorder or an atopic disorder. Examples of inflammatory disorders include but are not limited to chronic obstructive pulmonary disease, asthma, rheumatoid arthritis, inflammatory bowel disease (including Crohns disease and ulcerative colitis), multiple sclerosis, psoriasis, ischemia-reperfusion injuries, septic shock, age-related macular degeneration, atherosclerosis, Alzheimer's disease, cardiovascular disease, vasculitis, type I and II diabetes, metabolic syndrome, diabetic retinopathy, restenosis. Examples of autoimmune diseases include but are not limited to asthma, rheumatoid arthritis, inflammatory bowel disease, multiple sclerosis, psoriasis, type I diabetes, systemic lupus erythematosus (SLE), Sjögren's syndrome, Hashimoto's thyroiditis, Graves' disease, Guillain-Barré syndrome, autoimmune hepatitis, Myasthenia gravis. Examples of fibrotic diseases include but are not limited to scleroderma, chronic obstructive pulmonary disease, diabetic nephropathy, sarcoidosis, idiopathic pulmonary fibrosis, cirrhosis, cystic fibrosis, post-operative fibroids, and restenosis. Examples of atopic disease include but are not limited to atopic dermatitis, atopic asthma, and allergic rhinitis. The compositions of the invention are administered to a subject having or at risk of developing one or more of the diseases in an effective amount for treating the disorder or condition.

In a preferred embodiment, the subject has, or is at risk of having, a cancer or metastatic disorder (e.g., a carcinoma). For example, the subject has a primary tumor and has, or is at risk of having, a metastasis of that primary tumor.

In one embodiment, the polysaccharide preparation is administered intravenously or subcutaneously.

In one embodiment, the polysaccharide preparation is administered in combination with another therapy, e.g., another therapeutic agent, e.g., a cytotoxic or cytostatic agent, and combinations thereof.

In one embodiment, the polysaccharide preparation is administered chronically, e.g., at least twice over a specific period of time, e.g., at least twice during a period of six months. In one embodiment, a polysaccharide preparation is administered twice over a period of one week, two weeks, three weeks, one month, two months, three months, six months, one year, or even longer. The polysaccharide preparation can be administered daily (e.g., once, twice, or three or four times daily), once every other day, weekly (e.g., once, twice, or three times a week), once every other week, monthly, or any other chronic administration schedule.

A polysaccharide preparation that lacks substantial anticoagulant activity, as used herein, is one that has anti-Xa and anti-IIa activity each less than 100 IU/mg (e.g., less than 80 IU/mg, 70 IU/mg, or 60 IU/mg). In some embodiments, the polysaccharide preparation has substantially no anticoagulant activity, i.e., anti-Xa and anti-IIa activity each less than 50 IU/mg.

For any of the ranges described herein, e.g., for a given structure or activity, the ranges can be those ranges disclosed as well as other ranges. For example, a range constructed from a lower endpoint of one range, e.g., for a given building block or activity, can be combined with the upper endpoint of another range, e.g., for the given building block or activity, to give a range.

An "isolated" or "purified" polysaccharide preparation is substantially free of cellular material or other contaminating proteins from the cell or tissue source from which the polysaccharide is derived, or substantially free from chemical precursors or other chemicals when chemically synthesized. "Substantially free" means that a preparation is at least 50% pure (wt/wt). In a preferred embodiment, the preparation has less than about 30%, 20%, 10% and more preferably 5% (by dry weight), of non-heparin-derived polysaccharides, proteins or chemical precursors or other chemicals, e.g., from manufacture. These also referred to herein as "contaminants." Examples of contaminants that can be present in a polysaccharide preparation provided herein include, but are not limited to, calcium, sodium, heparinase enzyme (or other enzyme having similar substrate specificity), methanol, ethanol, chloride, sulfate, dermatan sulfate, and chondroitin sulfate.

Other features and advantages of the invention will be apparent from the following detailed description, and from the claims.

BRIEF DESCRIPTION OF THE DRAWINGS

FIG. 1 is a bar graph showing the effect of a polysaccharide preparation described herein in a murine melanoma experimental metastasis (B16F10 i.v.) model. Lung tumor burden (lung weight—normal lung weight) was determined for female C57BL/6 mice (9-10 weeks old) challenged with i.v. injection of $2 \times 10^5$ B16F10 cells and pretreated with a single dose (10 mg/kg) of MONC703 (batch R-6-1), dalteparin/Fragmin®, or MONC 202 (negative control, N-desulfated polysaccharide) immediately before injection. "Normal" designates unchallenged and untreated mice.

DETAILED DESCRIPTION

Optimized Polysaccharides

In many clinical settings, commercially available LMWH preparations are preferred over UFH preparations as anticoagulants because LMWHs have more predictable pharmacokinetics and can be administered subcutaneously. However, because of the potential for bleeding complications due to their anticoagulant effects, currently available LMWH preparations are less suitable for therapy of non-coagulation mediated disorders, and/or for disorders that may require higher doses or chronic dosing regimens. The invention features polysaccharide preparations designed to lack substantial anticoagulant activity while retaining clinically advantageous properties. Properties of the polysaccharide preparations include, e.g., lacking substantial anticoagulant activity, e.g., having substantially no anticoagulant activity (e.g., anti-IIa activity less than 50 IU/mg, anti-Xa activity less than 50 IU/mg), and having anti-metastatic, anti-angiogenic and/or anti-inflammatory activity.

Examples of such preparations include chains that include the following

—$U_{2S}$—$H_{x,y,z}$—[$U_w H_{x,y,z}$]$_n$ wherein n is an integer such that n=1-20; w=–2OS or –2OH; x=–NS or –NAc; y=–3OS or –3OH; z=–6OS or –6OH; wherein U indicates a uronic acid residue and H indicates a hexosamine residue; and wherein w, x, y, and z are the same or different on each U or H residue.

Anti-IIa Activity

Polysaccharide preparations are disclosed herein that provide substantially reduced anti-IIa activity, e.g., anti-IIa activity of about 0 to 50 IU/mg, e.g., about 0 to 40 IU/mg, about 0 to 30 µl/mg, about 0 to 25 µl/mg, about 0 to 20 IU/mg, about 0 to 10 IU/mg, about 5 to 10 IU/mg, about 5 to 15 IU/mg, about 5 to 20 IU/mg. Anti-IIa activity is calculated in International Units of anti-IIa activity per milligram using statistical methods for parallel line assays. The anti-IIa activity levels described herein are measured using the following principle.

Polysaccharide (PS)+ATIII→[PS·ATIII]

IIa

PS·ATIII→[PS·ATIII·IIa]+IIa (Excess)

IIa (Excess)+Substrate→Peptide+pNA (measured spectrophotometrically)

Anti-factor IIa activity is determined by the sample potentiating effect on antithrombin (ATIII) in the inhibition of thrombin. Thrombin excess can be indirectly spectrophotometrically measured. The anti-factor IIa activity can be measured, e.g., on a Diagnostica Stago analyzer or on an ACL Futura3 Coagulation system, with reagents from Chromogenix (S-2238 substrate, Thrombin (53 nkat/vial), and Antithrombin), or on any equivalent system. Analyzer response is calibrated using the 2nd International Standard for Low Molecular Weight Heparin.

Anti-Xa Activity

Preferably, a preparation provided herein has an anti-Xa activity of about 0 to 50 IU/mg, about 0 to 40 IU/mg, about 0 to 30 IU/mg, about 0 to 25 IU/mg, about 10 to 50 IU/mg, about 20 to 50 IU/mg, about 20 to 40 IU/mg, about 30 to 40 IU/mg. Anti-Xa activity of a preparation is calculated in International Units of anti-factor Xa activity per milligram using statistical methods for parallel line assays. The anti-factor Xa activity of preparations described herein is measured using the following principle:

PS+ATIII→[PS·ATIII]

FXa

PS·ATIII→[PS·ATIII·FXa]+FXa(Excess)

FXa (Excess)+Substrate→Peptide+pNA (measured spectrophotometrically)

The anti-factor Xa activity is determined by the sample potentiating effect on antithrombin (ATIII) in the inhibition of activated Factor Xa (FXa). Factor Xa excess can be indirectly spectrophotometrically measured. Anti-factor Xa activity can be measured, e.g., on a Diagnostica Stago analyzer with the Stachrom® Heparin Test kit, on an ACL Futura3 Coagulation system with the Coatest® Heparin Kit from Chromogenix, or on any equivalent system. Analyzer response can be calibrated using the NIBSC International Standard for Low Molecular Weight Heparin.

Molecular Weight and Chain Length

When weight average molecular weight of a preparation is determined, a weight average molecular weight of about 3500 to 7000 Da, about 3500 to 5500 Da, preferably about 4500 to 5500 Da or about 4500 to 5000 Da indicates that a significant number of chains in the polysaccharide preparation are of sufficient chain length.

"Weight average molecular weight" as used herein refers to the weight average in daltons of chains of uronic acid/hexosamine disaccharide repeats. The presence of non-uronic acid and/or non-hexosamine building blocks are not included in determining the weight average molecular weight. Thus, the molecular weight of non-uronic acid and non-hexosamine building blocks within a chain or chains in the preparation should not be included in determining the weight average molecular weight. The weight average molecular weight ($M_w$) is calculated from the following equation: $M_w = \Sigma(c_i m_i)/\Sigma c_i$. The variable $c_i$ is the concentration of the polymer in slice i and $m_i$ is the molecular weight of the polymer in slice i. The summations are taken over a chromatographic peak, which contains many slices of data. A slice of data can be pictured as a vertical line on a plot of chromatographic peak versus time. The elution peak can therefore be divided into many slices. The weight average molecular weight calculation is average dependant on the summation of all slices of the concentration and molecular weight. The weight average molar weight can be measured, e.g., using the Wyatt Astra software or any appropriate software. The weight average molecular weights described herein are determined by high liquid chromatography with two columns in series, for example a TSK G3000 SWXL and a G2000 SWXL, coupled with a multi angle light scattering (MALS) detector and a refractometric detector in series. The eluent used is a 0.2 M sodium sulfate, pH 5.0, and a flow rate of 0.5 mL/min.

A determination of whether a polysaccharide preparation includes chains of sufficient chain length can be made, for example, by determining the average chain length of the chains in the preparation and/or by determining the weight average molecular weight of chains within the preparation. When average chain length is determined, an average chain length of about 5 to 20, e.g., about 7 to 18, about 7 to 14, about 7 to 12, about 7 to 10, or about 8 to 10 disaccharide repeats, indicates that a significant number of chains in the preparation are of sufficient chain length.

"Average chain length" as used herein refers to the average chain length of uronic acid/hexosamine disaccharide repeats that occur within a chain. The presence of non-uronic acid and/or non-hexosamine building blocks (e.g., attached PEG moieties) are not included in determining the average chain length. Average chain length is determined by dividing the number average molecular weight (Mn) by the number average molecular weight for a disaccharide (500 Da). Methods of determining number average molecular weight are described below using SEC MALS.

Glycol Split Uronic Acids

A polysaccharide preparation described herein can include substantially no opening of the glycoside rings, conventionally called reduction-oxidation (RO) derivatives. RO derivatives have one or more glycoside rings that are opened, e.g., at the bond between C2 and C3.

Non-Reducing End Structure

A preparation described herein can have a mixture of ΔU and iduronic acid (I)/glucuronic acid (G) at the non-reducing end of the chains in the preparation. Preferably, about 60%, 70%, 80%, 90%, 95%, 98%, 99% or all of the polysaccharide chains of the preparation have a ΔU. The nomenclature "—U" refers to an unsaturated uronic acid (iduronic acid (I), glucuronic acid (G) or galacturonic acid) that has a double bond introduced at the 4-5 position as a result, e.g., of the lyase action of a heparinase, a HSGAG lyase, or other enzyme having similar substrate specificity. The quantity of ΔU and/or I/G at the non-reducing end of chains within the sample can be determined using, e.g., 2D-NMR. In such methods, the total number of chains having an acetylated hexosamine ($H_{NAc}$) at the reducing end and/or the number of open ring confirmations at the reducing end can be used to determine the total number of chains within the preparation. The total percentage of chains having a ΔU and/or I/G at the non-reducing end can be compared to the total number of chains in the preparation. In some embodiments of the preparations described herein, less than 90%, less than 95%, less than 98%, less than 99%, or none of the chains in the preparation have a sulfated ΔU at the non-reducing end.

Reducing End Structures

In some instances, less than 50%, e.g., no more than about 45%, 40%, 35%, 30%, 25%, 20%, 15%, 10%, or 5% of the chains in the preparation have a modified reducing end structure.

Polydispersity

The polydispersity of polysaccharide preparations provided herein is about 2.1 or less, e.g., about 1.6 to 2.1 (e.g., about 1.6 to 2.0, about 1.7 to 2.0, about 1.6 to 1.9, about 1.7 to 1.9).

The term "polydisperse" or "polydispersity" refers to the weight average molecular weight of a composition (Mw) divided by the number average molecular weight (Mn). The number average molecular weight (Mn) is calculated from the following equation: Mn=Σci/(Σci/ml). The variable ci is the concentration of the polysaccharide in slice i and Mi is the molecular weight of the polysaccharide in slice i. The summations are taken over a chromatographic peak, which contains many slices of data. A slice of data can be pictured as a vertical line on a plot of chromatographic peak versus time. The elution peak can therefore be divided into many slices. The number average molecular weight is a calculation dependent on the molecular weight and concentration at each slice of data. Methods of determining weight average molecular weight are described above, and were used to determine polydispersity as well.

Methods of Making Polysaccharide Preparations

Various methods of making polysaccharide preparations, e.g., a preparation described herein are also contemplated. For example, such methods include a method of making a polysaccharide preparation having an average chain length of about 7 to 18 disaccharides. The method includes providing a precursor heparin preparation having a chain length of greater than 7 to 18 disaccharides, and processing the precursor heparin preparation (e.g., by enzymatic or chemical depolymerization, e.g., by nitrous acid depolymerization) to obtain a polysaccharide preparation having an average chain length of about 7 to 18 disaccharides. Preferably, the precursor has an average chain length of about 7 to 14, e.g., 8 to 13, disaccharides. For example, the precursor heparin preparation can be unfractionated heparin.

The precursor heparin preparation can be processed by a method comprising depolymerization (e.g., enzymatic depolymerization). In one embodiment, a suitable enzyme is one that cleaves UFH at the pentasaccharide site ($H_{NAc/S,6S}GH_{NS,3S,6S}I_{2S}H_{NS,6S}$), optionally among other sites. In another embodiment, a suitable enzyme is one that cleaves a $I_{2S}H_{NS}$ or $I_{2S}H_{AC}$. For example, *Bacteroides thetaiotaomicron* Heparinase I can be used. Other enzymes can be identified by screening enzymes for the above abilities, e.g., as determined by 1D NMR, 2D NMR, HSQC-NMR, mass spectrometry, e.g., electrospray MS, MALDI-MS, LC-MS, or GPC-MS, or using Arixtra or another suitable polysaccharide as a control for enzyme activity and/or MALDI detection of the cleavage products.

Biological Activities

The preparations described herein have anti-metastatic activity as assayed in an animal model of metastasis in which B16F10 melanoma cells injected into the tail veins of C57/BL mice arrest in the lungs and proliferate as discrete pulmonary foci. This assay is generally described in Gabri et al., 2006, Clin. Cancer Res., 12:7092-98. A preparation may additionally have activity in other experimental models of metastasis, including the C170HM2 assay, in which C170HM2 human colorectal cancer line cells are injected into the peritoneal cavity, where the primary site of metastasis is to the liver. The preparations described herein may also show anti-metastatic activity in spontaneous models of metastasis, such as the AP5LV model, in which AP5LV human colorectal cancer cells are implanted into the peritoneal wall and exhibit spontaneous metastasis to the lung, or the 4T1 model, in which 4T1 murine mammary carcinoma cells implanted in to the mammary fat pad exhibit spontaneous metastasis to the lung and other organs.

The preparations described herein can bind to and/or modulate (e.g., inhibit) an activity of one or more of VEGF, FGF, SDF-1, and P-selectin binding/inhibition. In some embodiments, interaction of the preparation with (e.g., binding to) a target protein (e.g., VEGF, FGF, SDF-1, or P-selectin) can be assayed, e.g., in vitro, e.g., using methods known in the art. Numerous methods and techniques to detect binding or modulation (e.g., inhibition) of activity are known, e.g., standard receptor competition assays, fluorescence energy transfer (FET), fluorescence resonance energy transfer (FRET) (see, for example, U.S. Pat. No. 5,631,169; U.S. Pat. No. 4,868,103), and fluorescence polarization (FP). In some embodiments, evaluating binding of a polysaccharide preparation to a target protein can include a real-time monitoring of the binding interaction, e.g., using Biomolecular Interaction Analysis (BIA) (see, e.g., Sjolander and Urbaniczky (1991) Anal. Chem., 63:2338-2345 and Szabo et al. (1995) Curr. Opin. Struct. Biol., 5:699-705). Surface plasmon resonance or "BIA" detects biospecific interactions in real time, without labeling any of the interactants (e.g., BIAcore).

Activities of VEGF, FGF, and P-selectin on cells in vitro and in vivo are well known in the art. The ability of a polysaccharide preparation to modulate (e.g., inhibit) an activity of VEGF, FGF, or P-selectin can be assayed in vitro or in a cell-based assay or in vivo in an organism. For example, the ability of a polysaccharide preparation to modulate (e.g., inhibit) the activity of VEGF, FGF, or P-selectin to modulate (e.g., stimulate) the proliferation of endothelial cells, e.g., human umbilical vein epithelial cells, can be assayed. Exemplary methods of determining modulation of FGF activity can be found in U.S. Pat. No. 5,733,893. A cell-based assay can be performed using a single cell, or a collection of at least two or more cells. The cell can be a yeast cell (e.g., *Saccharomyces cerevisiae*) or a mammalian cell, e.g., a cell line.

Pharmaceutical Compositions

Compositions, e.g., pharmaceutically acceptable compositions, which include a preparation described herein, formulated together with a pharmaceutically acceptable carrier, are provided.

As used herein, "pharmaceutically acceptable carrier" includes any and all solvents, dispersion media, isotonic and absorption delaying agents, and the like that are physiologically compatible with parenteral administration. The carrier can be suitable for any parenteral administration, e.g., intravenous, intramuscular, subcutaneous, intraocular, rectal, inhaled or spinal administration (e.g., by injection or infusion).

The compositions of this invention may be in a variety of forms. These include, for example, liquid, semi-solid and solid dosage forms, such as liquid solutions (e.g., injectable and infusible solutions), dispersions or suspensions, and liposomes. The preferred form depends on the intended mode of administration and therapeutic application. Typical preferred compositions are in the form of injectable or infusible solutions. The preferred mode of administration is parenteral (e.g., intravenous, subcutaneous, intraocular, intraperitoneal, intramuscular). In a preferred embodiment, the preparation is administered by intravenous infusion or injection. In another preferred embodiment, the preparation is administered by intramuscular or subcutaneous injection.

The phrases "parenteral administration" and "administered parenterally" as used herein means modes of administration other than enteral and topical administration, usually by injection, and includes, without limitation, intravenous, intramuscular, subcutaneous, intraarterial, intrathecal, intracapsular, intraorbital, intravitreous, intracardiac, intradermal, intraperitoneal, transtracheal, subcutaneous, subcuticular, intraarticular, subcapsular, subarachnoid, intraspinal, epidural and intrasternal injection and infusion.

Therapeutic compositions typically should be sterile and stable under the conditions of manufacture and storage. The composition can be formulated as a solution, microemulsion, dispersion, liposome, or other ordered structure suitable to high concentration. Sterile injectable solutions can be prepared by incorporating the active compound (i.e., polysaccharide preparation) in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, the preferred methods of preparation are vacuum drying and freeze-drying that yields a powder of the active ingredient plus any additional desired ingredient from a previously sterile-filtered solution thereof. The proper fluidity of a solution can be maintained, for example, by the use of a coating such as lecithin, by the maintenance of the required particle size in the case of dispersion and by the use of surfactants. Prolonged absorption of injectable compositions can be brought about by including in the composition an agent that delays absorption, for example, various polymers, monostearate salts and gelatin.

For many therapeutic applications, the preferred route/mode of administration is intravenous injection or infusion. As will be appreciated by the skilled artisan, the route and/or mode of administration will vary depending upon the desired results.

Formulations for injection may be presented in unit dosage form, e.g., in ampoules, syringes, syringe pens, or in multi-dose containers, e.g., with an added preservative. The compositions may take such forms as suspensions, solutions or emulsions in oily or aqueous vehicles, and may contain formulatory agents such as suspending, stabilizing and/or dispersing agents.

For administration by inhalation, the preparation may be conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount. Capsules and cartridges of, e.g., gelatin for use in an inhaler or insufflator may be formulated containing a powder mix of the compound and a suitable powder base such as lactose or starch. In addition, dry powder formations for inhalation therapy are within the scope of the invention. Such dry powder formulations may be prepared as disclosed, e.g., in WO 02/32406.

In addition to the compositions described previously, the compounds may also be formulated as a depot preparation. Such long-acting formulations may be formulated with suitable polymeric or hydrophobic materials (for example, as an emulsion in an acceptable oil) or ion exchange resins, or as sparingly soluble derivatives, for example, as a sparingly soluble salt.

The pharmaceutical compositions also may comprise suitable solid or gel phase carriers or excipients.

The compositions can be included in a container, pack, or dispenser together with instructions for administration.

The preparation can also be administered with short or long term implantation devices, e.g., a stent. The preparation can be implanted subcutaneously, can be implanted into tissues or organs (e.g., the coronary artery, carotid artery, renal artery and other peripheral arteries, veins, kidney, heart cornea, vitreous, cerebrum, etc.), or can be implanted in physiological spaces around tissues and organs (e.g., kidney capsule, pericardium, thoracic or peritoneal space).

The preparation can also be used to coat various medical devices. For example, the preparation can be used to coat a stent or extracorporeal circuit. Such formulations of the preparations may include using, e.g., controlled release beads, gel or microspheres as well as various polymers such as PLGA, cellulose, alginate or other polysaccharides.

Dosage regimens are adjusted to provide the optimum desired response (e.g., a therapeutic response). For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the subjects to be treated; each unit contains a predetermined quantity of active compound calculated to produce the desired therapeutic effect in association with the required pharmaceutical carrier. The specification for the dosage unit forms of the invention are dictated by and directly dependent on (a) the unique characteristics of the active compound and the particular therapeutic effect to be achieved, and (b) the limitations inherent in the art of compounding such an active compound for the treatment of sensitivity in individuals.

It is to be noted that dosage values may vary with the type and severity of the condition to be alleviated. It is to be further understood that for any particular subject, specific dosage regimens should be adjusted over time according to the individual need and the professional judgment of the person administering or supervising the administration of the compositions.

The pharmaceutical compositions of the invention may include a therapeutically effective amount of a preparation. A therapeutically effective amount of the preparation may vary according to factors such as the disease state, age, sex, and weight of the individual and can include more than one unit dose. A therapeutically effective amount is also one in which any toxic or detrimental effects of the preparation are outweighed by the therapeutically beneficial effects. A therapeutically effective amount may inhibit a measurable parameter, e.g., VEGF activity, FGF activity, P-selectin activity, or size or rate of growth of metastatic lesions, e.g., by at least about 20%, more preferably by at least about 25%, 30%, 40%, even more preferably by at least about 50%, 60%, and still more preferably by at least about 70%, 80% relative to untreated subjects. The ability of a compound to inhibit a measurable parameter, e.g., metastasis or angiogenesis, can be evaluated in an animal model system or in a human (e.g., in a clinical trial). Alternatively, a property of a composition can be evaluated by examining the activity of the compound in an in vitro assay. Exemplary doses for intravenous administration of the polysaccharide preparation are about 0.03 mg/kg to 0.45 mg/kg, e.g., 0.03 mg/kg, 0.05 mg/kg, 0.1 mg/kg, 0.15 mg/kg, 0.2 mg/kg, 0.22 mg/kg, 0.25 mg/kg, 0.27 mg/kg, 0.3 mg/kg, 0.35 mg/kg, 0.37 mg/kg, 0.4 mg/kg, 0.44 mg/kg, preferably about 0.1 mg/kg, 0.15 mg/kg, 0.2 mg/kg, 0.25 mg/kg, 0.3 mg/kg, 0.35 mg/kg, 0.4 mg/kg, 0.44 mg/kg, 0.47 mg/kg, 0.5 mg/kg, 0.55 mg/kg, 0.60 mg/kg, 0.7 mg/kg, preferably about 0.30 to 0.50 mg/kg, e.g., 0.30 mg/kg, 0.35 mg/kg, 0.40 mg/kg, 0.42 mg/kg, 0.44 mg/kg, 0.47 mg/kg or 0.50 mg/kg.

Also within the scope of the invention are kits comprising a polysaccharide preparation provided herein. The kit can include one or more other elements including: instructions for use; other reagents, e.g., a therapeutic agent; devices or other materials for preparing the polysaccharide preparation for administration; pharmaceutically acceptable carriers; and devices or other materials for administration to a subject. The instructions can include instructions for therapeutic application including suggested dosages and/or modes of administration, e.g., in a patient having a disorder, e.g., a disorder described herein. The kit can further contain at least one additional reagent, such as a diagnostic or therapeutic agent, e.g., a diagnostic or therapeutic agent as described herein, formulated as appropriate, in one or more separate pharmaceutical preparations.

Uses

The polysaccharide preparations can be used to treat a subject. As used herein, a subject is a mammal, e.g., a non-human experimental mammal, a veterinary mammal, or a human. Non-human mammals include a primate, cow, horse, pig, sheep, goat, dog, cat, or rodent.

The preparations provided herein can be used, for example, to treat or prevent a metastatic disorder (e.g., a cancer, e.g., a carcinoma or other solid cancer). As used herein, the term "cancer" is meant to include all types of cancerous growths or oncogenic processes, metastatic tissues or malignantly transformed cells, tissues, or organs, irrespective of histopathologic type or stage of invasiveness. Methods and compositions disclosed herein are particularly useful for treating, or reducing the size, numbers, or rate of growth of, metastatic lesions associated with cancer.

Examples of cancers include, but are not limited to, solid tumors, soft tissue tumors, hematopoietic tumors and metastatic lesions. Examples of solid tumors include malignancies, e.g., sarcomas, adenocarcinomas, and carcinomas, of the various organ systems, such as those affecting lung, breast, lymphoid, gastrointestinal (e.g., colon), genitals and genitourinary tract (e.g., renal, urothelial, bladder cells), pharynx, CNS (e.g., neural or glial cells), skin (e.g., melanoma), and pancreas, as well as adenocarcinomas which include malignancies such as most colon cancers, rectal cancer, renal-cell carcinoma, liver cancer, non-small cell carcinoma of the lung, cancer of the small intestine and cancer of the esophagus. Methods and compositions disclosed herein are particularly useful for treating, e.g., reducing or delaying, metastatic lesions associated with the aforementioned cancers. In some embodiments, the patient will have undergone one or more of surgical removal of a tissue, chemotherapy, or other anti-cancer therapy and the primary or sole target will be metastatic lesions, e.g., metastases in the bone marrow or lymph nodes.

The methods of the invention, e.g., methods of treatment, can further include the step of monitoring the subject, e.g., for a change (e.g., an increase or decrease) in one or more of: tumor size; levels of a cancer marker, for a patient with cancer; the size or rate of appearance of new lesions, e.g., in a scan; the appearance of new disease-related symptoms; the size of soft tissue mass, e.g., a decreased or stabilization; quality of life, e.g., amount of disease associated pain, e.g., bone pain; or any other parameter related to clinical outcome. The subject can be monitored in one or more of the following periods: prior to beginning of treatment; during the treatment; or after one or more elements of the treatment have been administered. Monitoring can be used to evaluate the need for further treatment with the same preparation or for additional treatment with additional agents. Generally, a decrease in one or more of the parameters described above is indicative of the improved condition of the subject.

The preparations described herein can be administered to a subject in single or multiple doses to treat or prevent a metastatic or cancerous disorder, e.g., a cancerous disorder described herein.

The preparations described herein can also be used to treat inflammatory, autoimmune, fibrotic, fibroproliferative, atopic, or angiogenic disorders. Examples of inflammatory disorders include but are not limited to chronic obstructive pulmonary disease, asthma, rheumatoid arthritis, inflammatory bowel disease (including Crohns disease and ulcerative colitis), multiple sclerosis, psoriasis, ischemia-reperfusion injuries, septic shock, age-related macular degeneration, atherosclerosis, Alzheimer's disease, cardiovascular disease, vasculitis, type I and II diabetes, metabolic syndrome, diabetic retinopathy, restenosis. Examples of autoimmune diseases include but are not limited to asthma, rheumatoid arthritis, inflammatory bowel disease, multiple sclerosis, psoriasis, type I diabetes, systemic lupus erythematosus (SLE), Sjögren's syndrome, Hashimoto's thyroiditis, Graves' disease, Guillain-Barré syndrome, autoimmune hepatitis, Myasthenia gravis. Examples of fibrotic diseases include but are not limited to scleroderma, chronic obstructive pulmonary disease, diabetic nephropathy, sarcoidosis, idiopathic pulmonary fibrosis, cirrhosis, cystic fibrosis, post-operative fibroids, restenosis. Examples of atopic disease include but are not limited to atopic dermatitis, atopic asthma, and allergic rhinitis.

Examples of fibroproliferative disorders include systemic and local scleroderma, keloids and hypertrophic scars, atherosclerosis, restenosis, fibrosarcoma and rheumatoid arthritis. Examples of scarring associated with trauma include scarring due to surgery, chemotherapeutic-induced fibrosis, radiation-induced fibrosis, scarring associated with injury or burns.

In one embodiment, the polysaccharide preparations are used for inhibiting angiogenesis, e.g., to treat angiogenic disorders. Angiogenesis as used herein is the inappropriate formation of new blood vessels. Angiogenic disorders include, but are not limited to, tumors, neovascular disorders of the eye, endometriosis, macular degeneration, osteoporosis, psoriasis, arthritis, cancer and cardiovascular disorders.

The preparations described herein can also be used to treat or prevent infectious disorders such as, e.g., malaria.

It is understood that some disorders will fall within more than one category of disease described herein.

Combination Therapy

The methods and compositions of the invention can be used in combination with other therapeutic modalities. Administered "in combination", as used herein, means that two (or more) different treatments are delivered to the subject during the course of the subject's affliction with the disorder, such that the effects of the treatments on the patient overlap at a point in time. In some embodiments, the delivery of one treatment is still occurring when the delivery of the second begins, so that there is overlap in terms of administration. This is sometimes referred to herein as "simultaneous" or "concurrent delivery." In other embodiments, the delivery of one treatment ends before the delivery of the other treatment begins. In some embodiments of either case, the treatment is more effective because of combined administration. For example, the second treatment is more effective, e.g., an equivalent effect is seen with less of the second treatment, or the second treatment reduces symptoms to a greater extent, than would be seen if the second treatment were administered in the absence of the first treatment, or the analogous situation is seen with the first treatment. In some embodiments, delivery is such that the reduction in a symptom, or other parameter related to the disorder is greater than what would be observed with one treatment delivered in the absence of the other. The effect of the two treatments can be partially additive, wholly additive, or greater than additive. The delivery can be such that an effect of the first treatment delivered is still detectable when the second is delivered.

In one embodiment, the methods of the invention include administering to the subject a preparation described herein, in combination with one or more additional therapies, e.g., surgery, radiation therapy, or administration of another therapeutic preparation. In one embodiment, the additional therapy may include chemotherapy, e.g., a cytotoxic agent. In one embodiment the additional therapy may include a targeted therapy, e.g. a tyrosine kinase inhibitor, a proteasome inhibitor, a protease inhibitor. In one embodiment, the additional therapy may include an anti-inflammatory, anti-angiogenic, anti-fibrotic, or anti-proliferative compound, e.g., a steroid, a biologic immunomodulator, a monoclonal antibody, an antibody fragment, an aptamer, an siRNA, an antisense molecule, a fusion protein, a cytokine, a cytokine receptor, a steroid, a bronchodialator, a statin, an anti-inflammatory agent (e.g. methotrexate), an NSAID. In another embodiment, the additional therapy could include combining therapeutics of different classes. The polysaccharide preparation and the additional therapy can be administered simultaneously or sequentially.

Exemplary cytotoxic agents that can be administered in combination with the polysaccharide preparation include antimicrotubule agents, topoisomerase inhibitors, antimetabolites, mitotic inhibitors, alkylating agents, intercalating agents, agents capable of interfering with a signal transduction pathway, agents that promote apoptosis and radiation. In one embodiment, the cytotoxic agent that can be administered with a preparation described herein is taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, puromycin, and maytansinoids.

The combination therapy can also include a composition of the present invention coformulated with, and/or coadministered with, one or more additional therapeutic agents, e.g., one or more anti-cancer agents, cytotoxic or cytostatic agents, hormone treatment, vaccines, and/or other immunotherapies.

Other Embodiments

This invention is further illustrated by the following examples that should not be construed as limiting. The contents of all references, patents and published patent applications cited throughout this application are incorporated herein by reference.

EXAMPLES

Example 1

Preparation of a Polysaccharide Preparation

This example describes the production of a polysaccharide preparation described herein.
Method Overview:

Unfractionated Heparin (5 g) was dissolved in 50 mL of buffer (50 mM sodium acetate and 10 mM calcium acetate, pH 7.0) and equilibrated at 30° C. Subsequently, a suspension of the *Bacteroides thetaiotaomicron* Heparinase I (2.25 IU/g) was added to this reaction solution, and the reaction was allowed to stir for at least 16 hours while the temperature was maintained between 20-30° C. The degree of depolymerization in this reaction was monitored by measuring the absorbance at 232 nm ($UV_{232}$), and the reaction was quenched when the $UV_{232}$ reached an absorbance value of between 1.7 and 2.0. Subsequently, 5 g of sodium chloride was added to the reaction solution, followed by addition of methanol (150 mL) with constant stirring. The precipitate was allowed to age at 6° C. for 2-24 hours. This precipitate was then filtered and dried to yield the desired polysaccharide preparation in 75-80% yield. The polysaccharide preparation obtained was found to possess the following characteristics:

Mw: 4300-4900
Mw Distribution:
(i)<3000 Daltons: 36-45%
(ii) 3000-8000 Daltons: 42-50%
(iii)>8000 Daltons: 6-15%
Anti-Xa Activity: 25-40 IU/mg
Anti-IIa Activity: 5-15 IU/mg Example 2

Anti-Metastatic Properties of Polysaccharide Preparations

This example shows that the polysaccharide preparations have anti-cancer and anti-metastatic activity in multiple models of metastasis.

Model A: Murine Melanoma Experimental Metastasis (B16F10 iv) Model

A polysaccharide preparation produced as described in Example 1 (herein referred to as "MONC703") showed anti-metastasis activity in a murine melanoma experimental metastasis model.

Figure 1:
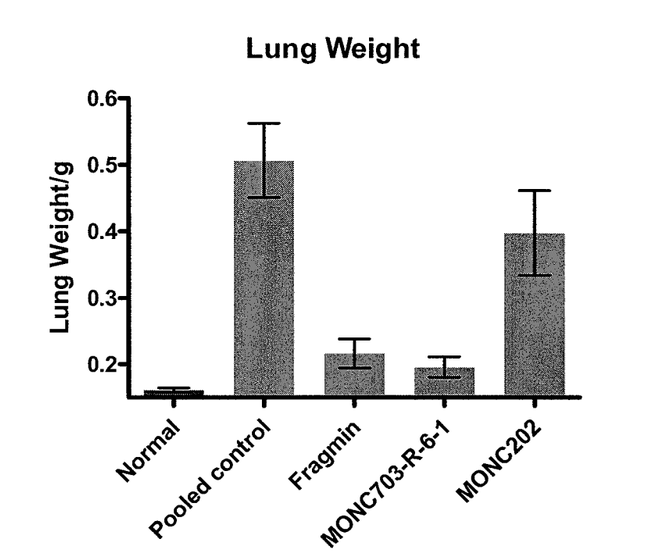

Female C57BL/6 mice (9-10 weeks old) were treated once with a single dose (10 mg/kg) of MONC703, dalteparin (Fragmin® (a LMWH which has been reported to have anti-metastatic activity), or MONC 202 (negative control, N-desulfated LMWH) immediately before i.v. injection of $2 \times 10^5$ B16F10 cells. Mice were sacrificed on day 21 and tumor burden was calculated as lung weight-normal lung weight. As shown in FIG. 1, MONC703 significantly inhibited B16F10 colonization of the lung relative to a pooled (untreated) control.

Model B: Colon Cancer Metastasis to the Liver

MONC703 showed anti-metastasis activity in an orthotopic liver metastasis model.

Liver metastasis was initiated by intraperitoneal injection of C170HM2 human colorectal tumor cells into male MF1 nude (nu/nu) athymic mice. 5FU/leucovorin was used as a positive control.

C170HM2 cells were maintained in vitro in RPMI culture medium (Sigma) containing 10% (v/v) heat inactivated fetal bovine serum and 2 mM L-glutamine at 37° C. in 5% $CO_2$ and humidified conditions. Cells from sub-confluent monolayers were harvested with 0.025% EDTA, washed in culture medium and re-suspended in sterile phosphate buffered saline, pH 7.4 (PBS) for in vivo administration. $1.5 \times 10^6$ cells in a volume of 1 ml were injected intraperitoneally into 65 mice, and the mice were allocated into treatment groups as below.

| Group 1: n = 10 | Vehicle control |
|---|---|
| Group 2: n = 10 | 25 mg/kg 5 FU/leucovorin i.v. cycled on days 1, 3, 5, 7 |
| Group 3: n = 10 | 5 mg/kg compound 1 (Dalteparin) s.c. once daily |
| Group 4: n = 10 | 5 mg/kg compound 3 (M703) s.c. once daily |
| Group 5: n = 10 | 15 mg/kg compound 3 s.c. once daily |
| Group 6: n = 10 | 30 mg/kg compound 3 s.c. once daily |
| Group 7: n = 5 | Untreated |

Treatment was initiated on day 1 following cell injection and continued until day 35 or until the clinical condition of the animal required termination. One mouse in group 6 was terminated on day 20 due to black tail, bruising, and very pale appearance. Groups and 6 missed one dose on day 5. No adverse affects of the test compounds in mice bearing the tumors were observed.

The study was terminated on day 35, and the tumors in the liver were excised and weighed. The mean liver tumor weights and cross-sectional area are summarized in Table 2.

TABLE 2

Summary of mean liver tumor weight and statistical analysis

| | | Mean tumor weight | | | Mean tumor area | | |
|---|---|---|---|---|---|---|---|
| Group | Treatment | (g) | (% of vehicle) | One way ANOVA | (mm²) | (% of vehicle) | One way ANOVA |
| 1 | Vehicle | 0.097 | 100.00 | — | 34.18 | 100.00 | — |
| 2 | 5 FU/Leu | 0.037 | 11.94* | p = 0.006* | 13.12 | 15.7 | p = 0.011 |
| 3 | 5 mg/kg Dalteparin | 0.018 | 18.56 | p = 0.017 | 8.09 | 23/67 | p = 0.031 |
| 4 | 5 mg/kg M703 | 0.134 | 138.14 | NS | 45.63 | 133.5 | NS |
| 5 | 15 mg/kg M703 | 0.151 | 155.67 | NS | 40.79 | 119.34 | NS |
| 6 | 30 mg/kg M703 | 0.019 | 19.59 | p = 0.026 | 8.86 | 25.92 | p = 0.049 |
| 7 | Untreated control | 0.31 | — | p = 0.035 | 83.58 | 244.53 | p = 0.084 |

*Statistical analysis and % of control for group 2 were calculated in comparison to group 7, not group 1.
NS = not significant 30 mg/kg of M703 significantly reduced the tumor size by approximately 80% (p=0.017) when compared to the vehicle control group. Dalteparin reduced liver tumor weight by approximately 81% (p=0.017) when compared to the vehicle control group. Similarly, the cross-sectional area of the tumors also showed significant reduction with 30 mg/kg M703 (p=0.049), and with dalteparin (p=0.027).

The positive control 5FU/leucovorin (group 2) significantly decreased the tumor weight in the liver by approximately 88% (p=0.006, or alternatively 84% decrease in tumor cross-sectional area measured, p=0.011) when compared to the untreated control group (group 7). However, when compared to the vehicle control group (group 1), the decrease in tumor size was 62% and not significant. It was observed that the liver tumor size in the vehicle control group was 69% smaller than that measured in the untreated group (difference in tumor weight was significant). This was possibly due to the handling of the mice on a daily basis from an early stage in order to administer the doses in the treatment groups, which may have reduced the tumor take within the liver.

Mouse weights were monitored for the duration of the study. The mouse weights for each group remained within an acceptable range for all groups throughout the study.

This example demonstrates the anti-metastatic properties of the polysaccharide preparations described herein.

What is claimed is:

1. A pharmaceutical composition comprising a low molecular weight heparin preparation and a pharmaceutically acceptable carrier, wherein the low molecular weight heparin preparation is produced by a process comprising digesting unfractionated heparin (UFH) with a heparinase that cleaves at the pentasaccharide site comprising:

(1) digesting UFH with *Bacteroides thetaiotaomicron* Heparinase I;

(2) monitoring absorbance at 232 nm during the step of digesting; and (3) quenching the digestion reaction when the absorbance at 232 nm reaches between 1.7 and 2.0, wherein the low molecular weight heparin preparation has an anti-Xa activity of 10-40 IU/mg and an anti-IIa activity of 5-15 IU/mg, a weight average molecular weight between 3,500 and 5,500 and a molecular weight distribution such that 30-50% of the oligosaccharides of the preparation have a molecular weight <3000 Da; 40-55% of the oligosaccharides have a molecular weight between 3000-8000 Da, and 5-30% of the oligosaccharides have a molecular weight >8000 Da, wherein the preparation has no glycol split uronic acid residues, and wherein the preparation consists essentially of polysaccharides of Formula I:

wherein n is an integer such that n=1-20;
w=–2OS or –2OH;
x=—NS or —NAc;
y=–3OS or –3OH;
z=–6OS or –6OH;
wherein U indicates a uronic acid residue and H indicates a hexosamine residue;
and wherein w, x, y, and z are independently the same or different on each U or H residue.

2. The pharmaceutical composition of claim 1, wherein the Heparinase I is present at about 1.0 to 5.0 IU/g UFH.

3. The pharmaceutical composition of claim 1, wherein the step of digesting does not include treatment with a thiol reducing agent.

4. The pharmaceutical composition of claim 1, wherein the preparation has an anti-Xa activity less than 40, 30, or 20 IU/mg.

5. The pharmaceutical composition of claim 1, wherein the low molecular weight heparin preparation has an anti-IIa activity of 5 to less than 10 IU/mg.

6. The pharmaceutical composition of claim 1, wherein the preparation has polysaccharide chains having greater than 40% $U_{2S}H_{NS,6S}$ disaccharide residues.

7. The pharmaceutical composition of claim 1, wherein the preparation has polysaccharide chains having greater than 50% $U_{2S}H_{NS,6S}$ disaccharide residues and a degree of desulfation less than 40%.

8. The pharmaceutical composition of claim 7, wherein the polysaccharides of the preparation have greater than 50% $U_{2S}H_{NS,6S}$ disaccharide residues.

9. The pharmaceutical composition of claim 7, wherein the polysaccharides of the preparation have greater than 60% $U_{2S}H_{NS,6S}$ disaccharide residues.

10. The pharmaceutical composition of claim 7, wherein the polysaccharides of the preparation have greater than 70% $U_{2S}H_{NS,6S}$ disaccharide residues.

11. The pharmaceutical composition of claim 7, wherein the polysaccharides of the preparation have greater than 80% $U_{2S}H_{NS,6S}$ disaccharide residues.

12. The pharmaceutical composition of claim 7, wherein the polysaccharides of the preparation have a degree of desulfation less than 30%.

13. The pharmaceutical composition of claim 12, wherein the polysaccharides of the preparation have a degree of desulfation less than 20%.

14. The pharmaceutical composition of claim 13, wherein the polysaccharides of the preparation have a degree of desulfation less than 10%.

15. The pharmaceutical composition of claim 1, wherein less than 2% of the polysaccharide chains of the preparation comprise the tetrasaccharide $UH_{NAc,6S}GH_{NS,3S,6S}$.

16. The pharmaceutical composition of claim 1, wherein about 20-30% of the polysaccharide chains of the preparation comprise the pentasaccharide $H_{NAc,6S}GH_{NS,3S,6S}I_{2S}H_{NS,6S}$.

17. The pharmaceutical composition of claim 1, wherein about 20-30% of the polysaccharide chains of the preparation comprise the tetrasaccharide $U_{2S}H_{NAc,6S}GH_{NS,3S,6S}$.

18. The pharmaceutical composition of claim 1, wherein the preparation has a polydispersity of about 1.6 to 2.1.

19. The pharmaceutical composition of claim 1, wherein the preparation has anti-metastatic activity.

20. The pharmaceutical composition of claim 1, wherein the preparation binds to one or more of: VEGF, FGF, SDF-1, or P-selectin.

21. The pharmaceutical composition of claim 20, wherein the preparation inhibits an activity of one or more of: VEGF, FGF, SDF-1, or P-selectin.

* * * * *